(12) United States Patent
De Faveri et al.

(10) Patent No.: US 10,329,264 B2
(45) Date of Patent: Jun. 25, 2019

(54) PROCESS FOR THE PREPARATION OF ISOCARBOXAZID

(71) Applicant: Lundbeck Pharmaceuticals Italy S.P.A., Padua (IT)

(72) Inventors: Carla De Faveri, Farra di Soligo TV (IT); Florian Anton Martin Huber, Dolo VE (IT); Nicola Antolini, Tione di Trento TN (IT)

(73) Assignee: Lundbeck Pharmaceuticals Italy S.P.A., Padua (IT)

( * ) Notice: Subject to any disclaimer, the term of this patent is extended or adjusted under 35 U.S.C. 154(b) by 0 days.

(21) Appl. No.: 15/748,209

(22) PCT Filed: Jul. 27, 2016

(86) PCT No.: PCT/EP2016/067868
§ 371 (c)(1),
(2) Date: Jan. 29, 2018

(87) PCT Pub. No.: WO2017/021246
PCT Pub. Date: Feb. 9, 2017

(65) Prior Publication Data
US 2018/0215722 A1    Aug. 2, 2018

(30) Foreign Application Priority Data

Jul. 31, 2015  (IT) .............. UB2015A2705

(51) Int. Cl.
*C07D 261/18*  (2006.01)
*B01D 9/00*    (2006.01)
*C07B 43/06*   (2006.01)
*C07B 63/00*   (2006.01)

(52) U.S. Cl.
CPC ......... *C07D 261/18* (2013.01); *B01D 9/0054* (2013.01); *C07B 43/06* (2013.01); *C07B 63/00* (2013.01)

(58) Field of Classification Search
CPC .................................................. C07D 261/18
See application file for complete search history.

(56) References Cited

U.S. PATENT DOCUMENTS 2,908,688 A    10/1959  Gardner et al.
6,518,254 B1 *  2/2003  Niemczyk ............ C07D 249/04
                                                    514/42

FOREIGN PATENT DOCUMENTS

EP    2016/067868    9/2016

OTHER PUBLICATIONS

International Search Report and Written Opinion dated Sep. 13, 2016 in connection with PCT/EP2016/067868.
Van Arnum et al., The Boulton-Katritzky rearrangement of isocarboxazid. J of Heterocyclic Chemistry. Sep. 2, 2009;46(5):909-913.

* cited by examiner

*Primary Examiner* — Golam M Shameem
(74) *Attorney, Agent, or Firm* — Wolf, Greenfield & Sacks, P.C.

(57) ABSTRACT

This invention relates to a novel chemical process for the synthesis of N'-benzyl-5-methylisoxazole-3-carbohydrazide (Isocarboxazid) which comprises reacting 5-methyl-3-isoxazole carboxylic acid ester with benzylhydrazine or a salt thereof in an aprotic organic solvent and in the presence of an organic base.

15 Claims, No Drawings

PROCESS FOR THE PREPARATION OF ISOCARBOXAZID

CROSS-REFERENCE TO RELATED APPLICATIONS

This application is a national stage filing under 35 U.S.C. § 371 of International Application No. PCT/EP2016/067868, filed Jul. 27, 2016, which claims priority to Italian Application No. UB2015A002705, filed Jul. 31, 2015, the entire contents of each of which are incorporated herein by reference.

This invention relates to a novel chemical process for the synthesis of N'-benzyl-5-methylisoxazole-3-carbohydrazide (Isocarboxazid).

BACKGROUND

N'-benzyl-5-methylisoxazole-3-carbohydrazide, which is known by the INN name Isocarboxazid, is a monoamine oxidase (MAO) inhibitor used for the treatment of depression, especially depressions that do not respond to other drugs.

Isocarboxazid, having the following chemical formula (I):

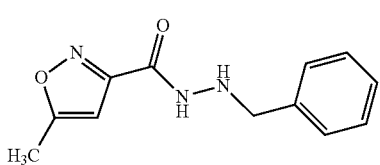

(I)

and CAS RN 59-63-2, is marketed under the brand name Marplan©.

U.S. Pat. No. 2,908,688 describes a process for making Isocarboxazid by reacting, in absence of any solvent, methyl 5-methylisoxazole-3-carboxylate with benzyl hydrazine at a temperature in the range from 60° to 100° C. The crude Isocarboxazid so obtained was extensively purified, initially by crystallisation in methanol followed by preparation of its hydrochloride salt, which was successively re-crystallised.

U.S. Pat. No. 6,518,254 discloses a process for preparing Isocarboxazid by adding benzylhydrazine to a solution of methyl 5-methylisoxazole-3-carboxylate in isopropanol, at a temperature of 45° C. The compound was obtained in molar 38% yield by filtration at 10° C. and treatment with cold isopropanol.

The above processes, due to one or more reasons, e.g. unfavourable impurity profile, multiple steps, low yield and difficult isolation procedures are not particularly convenient and suitable for industrial scale production.

Thus, there is an apparent need to develop improved processes for the preparation of substantially pure Isocarboxazid, which may be cost-effective, industrially amenable, with good % of yield and which may overcome the drawbacks of various prior disclosed processes.

SUMMARY OF THE INVENTION

The present invention provides a novel industrially applicable process for the preparation of Isocarboxazid, with a suitable impurity profile.

Particular aspects of the present invention relate to a process for the preparation of substantially pure N'-benzyl-5-methylisoxazole-3-carbohydrazide (Isocarboxazid).

Specifically, it has been found that the reaction of a 5-methylisoxazole-3-carboxylatic acid ester with benzylhydrazine in an aprotic solvent affords Isocarboxazid with a suitable impurity profile and without requirement of any additional purification steps.

Thus, the present process for the preparation of Isocarboxazid allows for a better control of impurity levels, higher yield and has fewer steps providing better cost of goods.

In one aspect, the present invention provides a process for the preparation of Isocarboxazid, which comprises:

a) reacting 5-methyl-3-isoxazole carboxylic acid ester (II)

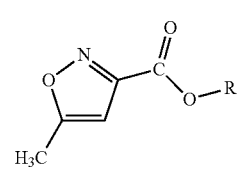

(II)

wherein, R is a $C_{1-4}$ alkyl
with benzylhydrazine or a salt thereof (III),

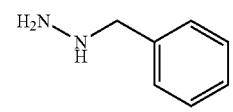

(III)

in an aprotic organic solvent, and in the presence of an organic base.

In a further embodiment, the invention provides a process for the preparation of Isocarboxazid which comprises:

a) reacting 5-methyl-3-isoxazole carboxylic acid ester (II),

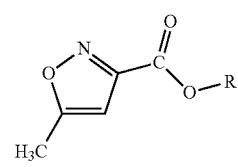

(II)

wherein R is a $C_{1-4}$ alkyl,
with benzylhydrazine (III) or a salt thereof

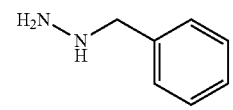

(III)

in an aprotic organic solvent and in the presence of an organic base, b) isolating the material as Isocarboxazid (I) and optionally c) re-crystallising the product of step (b).

Another aspect of the invention is a process for preparing a pharmaceutical composition comprising Isocarboxazid, characterized in that said Isocarboxazid is prepared by a process according to the present invention.

Definitions

In the present context, "benzylhydrazine (III) or a salt thereof" indicates benzylhydrazine on its free base form or an acid addition salt which may for example be selected from hydrochloride, oxalate, hydrobromide, hydroiodide, sulphate, p-toluenesulfonate (tosylate) or maleate. Particular mention is made of benzylhydrazine hydrochloride, such as benzylhydrazine dihydrochloride and benzylhydrazine monohydrochloride, and of benzylhydrazine oxalate. Within the scope is all possible stoichiometric and non stoichiometric forms of the salts of the compound (III). When a molar ratio is calculated between benzylhydrazine of formula (III) and ester of formula (II), said molar ratio is based on the molecular weigh of the free base form of benzylhydrazine. The same applies when a molar ratio is calculated between the organic base and benzylhydrazine of formula (III).

The term "$C_{1-4}$ alkyl" as used herein as a group or a part of the group refers to a linear or branched saturated hydrocarbon group containing from 1 to 4 carbon atoms. Examples of such groups include methyl, ethyl, n-propyl, isopropyl, n-butyl, isobutyl, sec-butyl, tert butyl.

The term "substantially pure Isocarboxazid" as used herein refers to Isocarboxazid having purity higher than 99%. Particularly, purity in the range of 99.5% to 99.9%.

The term "%" as used herein refers to area percentage by HPLC A/A.

The term "Volumes" as used herein refers to a volume of solvent per unit of 5-methyl-3-isoxazole carboxylic acid ester (II), thus, for example, 1 volume is 1 liter (Lt) per 1 kilogram (kg), 1 milliliter (ml) per 1 gram (g) or 1 microliter (μl) per 1 milligram (mg). Thus, 10 volumes mean for example 10 liters per 1 kilogram of 5-methyl-3-isoxazole carboxylic acid ester (II).

As used herein, the term "aprotic solvent" refers to any aprotic solvents including aromatic solvents such as toluene, chlorobenzene and xylene (single isomers and mixtures); alkanes and cycloalkanes such as heptane, hexane, cyclohexane and methylcyclohexane; esters such as ethylacetate and isopropylacetate; ethers such as diethylether, tert-butylmethylether, di-isopropylether, tetrahydrofuran, methyl-tetrahydrofuran and anisole; and mixtures thereof.

The term "heptane" includes n-heptane and its isomers such as 2-methylhexane (isoheptane), 3-methylhexane, 2,2-dimethylpentane, 2,3-dimethylpentane, 2,4-dimethylpentane, 3,3-dimethylpentane, 3-ethylpentane and 2,2,3-trimethylbutane; and mixtures thereof.

The term "hexane" includes n-hexane and its isomers such as 2-methylpentane, 3-methylpentane, 2,2-dimethylbutane and 2,3-dimethylbutane; and mixtures thereof.

The term "organic base" refers to any substance that can act as a proton acceptor. The base may for example be selected from triethylamine (TEA), diisopropyl ethyl amine (DIPEA), N-methylmorpholine, pyridine or 4-dimethylaminopyridine (DMAP).

DETAILED DESCRIPTION OF THE INVENTION

The present invention provides, in a first aspect, a process for the preparation of Isocarboxazid which comprises:

a) reacting 5-methyl-3-isoxazole carboxylic acid ester (II),

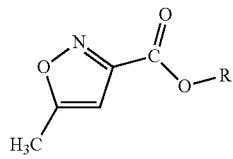
(II)

wherein R is a $C_{1-4}$ alkyl,
with benzylhydrazine (III) or a salt thereof

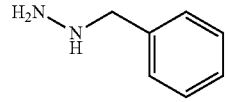
(III)

in an aprotic organic solvent and in the presence of an organic base.

The compounds of formula (II) and (III) are commercially available compounds.

In a one embodiment, the invention provides a process for the preparation of Isocarboxazid which comprises:

a) reacting 5-methyl-3-isoxazole carboxylic acid ester (II),

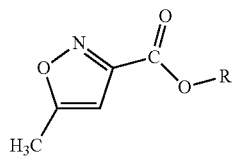
(II)

wherein R is a $C_{1-4}$ alkyl,
with benzylhydrazine (III) or a salt thereof

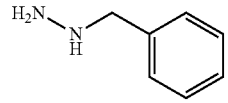
(III)

in an aprotic organic solvent and in the presence of an organic base, b) isolating the material as Isocarboxazid (I) and optionally c) re-crystallising the product of step (b).

In one embodiment of the invention, R is methyl.

In one embodiment, the reaction is performed at a temperature below 50° C., such as in the range of 25-50° C., such as in the range of 25-35° C.

In one embodiment, the compound (III) is benzylhydrazine dihydrochloride or benzylhydrazine monohydrochloride.

In one embodiment of the present invention, the ratio of benzylhydrazine of formula (III) and ester of formula (II) is in the range of 1.2 to 1.6 mol/mol. In a preferred embodiment, the ratio of benzylhydrazine (III) and ester of formula (II) is about 1.5 mol/mol.

In one embodiment of the invention, the ratio between the organic base and benzylhydrazine of formula (III) is in the range of 1.9 to 2.2 mol/mol. In one embodiment, the organic base is triethylamine. In a preferred embodiment, the ratio between triethylamine and benzylhydrazine (III) is in the range of 2.00-2.03 mol/mol.

In a particular embodiment, the invention provides a process for the preparation of Isocarboxazid which comprises:

a) reacting 5-methyl-3-isoxazole carboxylic acid methyl ester (II)

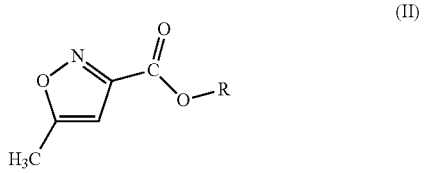

wherein R is methyl,
with benzylhydrazine (III) as a dihydrochloride or monochloride salt or a mixture thereof

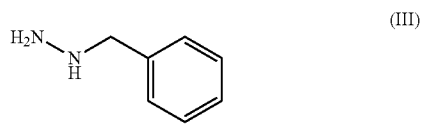

in an aprotic organic solvent selected from heptane or cyclohexane at a temperature in the range of 25-50° C. and in the presence of triethylamine, In one embodiment, the organic base is present in the range of 2.85 and 3.25 molar equivalents relative to compound II.

In one embodiment, the total amount of solvent is present in the range of 8 to 15 Volumes.

In one embodiment, the reaction time is in the range of 1.5 to 20 hours.

In a particular preferred embodiment, the process according to the invention is carried out in n-heptane and in the presence of triethylamine at a temperature in the range of 25 to 35° C., wherein the amount of solvent is present in the range of 8 to 15 Volumes; the ratio between triethylamine and benzylhydrazine (III) is in the range of 2.00 to 2.03 mol/mol and the ratio of benzylhydrazine (III) and ester of formula (II) is 1.5 mol/mol.

In a further embodiment, the Isocarboxazid (I) obtained in step a) is precipitated from the reaction mixture and can be isolated by filtration.

Performing the reaction of 5-methyl-3-isoxazole carboxylic acid methyl ester with benzylhydrazine obtained in situ, at a temperature below 50° C. and in an aprotic solvent, such as for example heptane, methylcyclohexane or cyclohexane or a mixture thereof, results in a significant higher yield of the Isocarboxazid compared with the prior art processes discussed above.

Advantageously, according to the process of the present invention, substantially pure end product Isocarboxazid (step (b)) is obtained and there is no requirement of any additional purification since it complies with the purity requirements of the drug substance requested by US Food and Drug Administration (FDA) and the European Medicinal Agency (EMA) as well as by the relative pharmacopoeia.

The product of step (b) may be optionally re-crystallised with the aim to adjust its particle size for drug formulation purposes, using standard procedures known in the art, such as cooling crystallisation or anti-solvent addition crystallisation. Thus, in a further aspect of the invention, the process further comprises re-crystallising the isolated Isocarboxazid (I).

In anti-solvent addition crystallisation, the product obtained in step (b) is dissolved in a minimum amount of suitable solvent, such as for example acetone, methanol, acetic acid or dimethylsulfoxide (DMSO) or a mixture thereof at a temperature in the range of 20 and 40° C.

Isocarboxazid may be isolated in a crystalline form by the addition of an anti-solvent such as for example water, toluene, isopropanol (IPA), alkanes such as heptane, or cycloalkanes such as cyclohexane, or a mixture thereof. A particular anti-solvent of use for the present process is a mixture of water and an alcohol such as isopropanol (IPA).

In one embodiment, the anti-solvent addition crystallisation is carried out at a temperature in the range of 20 and 25° C.

Optionally, prior to the addition of anti-solvent the solution is filtered. Optionally, prior to the addition of anti-solvent, the solution is treated with a charcoal and then filtered.

After crystallisation, the crystals can be isolated by filtration, washed using a suitable solvent, such as water, and dried under vacuum.

This disclosure is also directed, in part, to pharmaceutical compositions comprising Isocarboxazid prepared by the disclosed processes. In one embodiment, Isocarboxazid prepared by the above processes may be included in pharmaceutical compositions. These compositions may also comprise one or more conventional pharmaceutically acceptable carriers.

The carrier and the amounts of Isocarboxazid to be administered are well known to those skilled in the art. Thus for example, pharmaceutical compositions may include solid dosage forms. Solid dosage forms may include, for example, capsules, tablets, pills, powders, granules or any other suitable solid dosage form. In such solid dosage forms, Isocarboxazid (Compound (I)) may be combined with one or more pharmaceutically acceptable carriers.

If administered orally, Compound(I) may be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, polyvinyl alcohol or any other suitable excipient, and then tableted or encapsulated for convenient administration. Such capsules or tablets may contain a controlled-release formulation, as can be provided in, for example, a dispersion of the compound or salt in hydroxypropylmethyl cellulose. In the case of capsules, tablets, and pills, the dosage forms may also comprise buffering agents, such as sodium citrate, or magnesium or calcium carbonate, bicarbonate or any other suitable buffering agent. Tablets and pills may additionally be prepared with enteric coatings.

Thus, another aspect of the invention is a process for preparing a pharmaceutical composition comprising Isocarboxazid, characterized in that Isocarboxazid is prepared by a process according to the present invention.

A pharmaceutical composition comprising Isocarboxazid of the invention and a pharmaceutically acceptable carrier constitutes another aspect of the invention.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect of the invention using terms such as "comprising", "having," "including," or "containing" with reference to an element or elements is intended to provide support for a similar aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

EXPERIMENTAL SECTION

The invention is illustrated by the Examples described below. The examples are not intended to limit the scope of the invention. Various modifications and embodiments can be made without departing from the scope and spirit of the invention, which is defined by the following claims only.

Abbreviations

HPLC High Performance Liquid Chromatography
NMR Nuclear Magnetic Resonance

HPLC analyses indicated by HPLC, were performed with Waters Acquity instrument using a HALO C-18, 150×4.6 mm, 2.7 μm column under the following conditions:
Mobile phase A: Acetonitrile/TFA buffer (pH 3) 5/95;
Mobile phase B: Acetonitrile/TFA buffer (pH 3) 80/20;
TFA buffer (pH 3) preparation: in 1000 ml of Milli-Q water add trifluoroacetic acid (TFA) until pH=3.00±0.05;
Column temperature: 40° C.; Detector UV at 235 nm; Flow: 1.25 ml/min; Injection volume: 5 μl; Time of analysis: 26 minutes. RT Isocarboxazid=8.7 min.
Gradient:

| Time (min) | Mobile Phase A | Mobile Phase B |
|---|---|---|
| 0.0 | 100 | 0 |
| 5.5 | 70 | 30 |
| 8.0 | 70 | 30 |
| 17.0 | 0 | 100 |
| 20.0 | 0 | 100 |
| 21.0 | 100 | 0 |
| 26.0 | 100 | 0 |

$^1$H-NMR spectra were recorded at 20° C. on a Bruker Avance 300, operating at 300 MHz.

Chemical shifts are reported in ppm (δ) using the residual deuterated solvent line as internal standard.

Splitting patterns are designed as s, singlet; d, doublet; t, triplet; q, quartet; m, multiplet.

Sample preparation: weight about 10 mg of sample and dissolve it in a NMR 5 mm tube with about 0.5 ml of DMSO-d6.

Example 1

Preparation of
N'-benzyl-5-methylisoxazole-3-carbohydrazide
(Isocarboxazid)

Method A

A reactor was charged at room temperature with methyl 5-methylisoxazole-3-carboxylate (100 g), benzylhydrazine dihydrochloride (220.6 g, potentiometric assay of 94%) and n-heptane (800 ml). To the suspension was added slowly with a dropping funnel triethylamine (215.1 g). At the end of the addition the temperature was adjusted to about 30-31° C. and maintained at 30-33° C. for about 1.5 hours. An in-process control sample was taken to check the conversion: methyl 5-methylisoxazole-3-carboxylate was not detected. The suspension was cooled to 26° C. and water (400 ml) was added slowly with a dropping funnel (temperature at the end of the addition was 24° C.). The suspension was filtered and washed with water (2×100 ml) and n-heptane (2×100 ml). The product was dried under vacuum overnight at 45° C. and Isocarboxazid (135 g, molar yield of 82%, purity by HPLC 99.9%) was obtained as white solid.

Method B

A reactor was charged at room temperature with methyl 5-methylisoxazole-3-carboxylate (30 g), benzylhydrazine dihydrochloride (62.2 g, potentiometric assay of 100%) and n-heptane (450 ml). To the suspension was added slowly with a dropping funnel triethylamine (65.6 g). At the end of the addition the temperature was adjusted to about 25° C. and maintained at that temperature overnight. An in-process control sample taken after about 18 hours showed less than 1% of methyl 5-methylisoxazole-3-carboxylate. Water (180 ml) was added slowly with a dropping funnel. The suspension was filtered and washed with water (2×90 ml), isopropanol (2×63 ml) and n-heptane (2×63 ml). The product was dried under vacuum overnight at 30° C. and Isocarboxazid (39.5 g, molar yield of 80% purity by HPLC 99.7%) was obtained as an off-white solid.

Method C

A reactor was charged at room temperature with methyl 5-methylisoxazole-3-carboxylate (30 g), benzylhydrazine dihydrochloride (62.8 g, potentiometric assay of 99%) and n-heptane (450 ml). To the suspension was added slowly with a dropping funnel triethylamine (65.6 g). At the end of the addition the temperature was adjusted to about 35° C. and maintained at that temperature overnight. An in-process control sample taken after about 16 hours showed only 0.2% of methyl 5-methylisoxazole-3-carboxylate. The suspension was cooled to 20° C. and water (120 ml) was added slowly with a dropping funnel. The suspension was filtered and washed with water (2×60 ml) and n-heptane (2×60 ml). The product was dried under vacuum at 50° C. and Isocarboxazid (45.5 g, molar yield of 93%, purity by HPLC 99.1%) was obtained as white solid.

Method D

A reactor was charged at room temperature with methyl 5-methylisoxazole-3-carboxylate (5 g), benzylhydrazine dihydrochloride (11 g, potentiometric assay of 94%) and cyclohexane (50 ml). To the suspension was added slowly with a dropping funnel triethylamine (10.7 g). At the end of the addition the temperature was adjusted to about 30° C. and maintained at that temperature overnight. An in-process control sample taken after about 17.5 hours did not detect residual methyl 5-methylisoxazole-3-carboxylate. Water (20 ml) was added slowly with a dropping funnel. The suspension was filtered and washed with water (2×10 ml) and cyclohexane (2×10 ml). The product was dried under vacuum for 24 hours at 45° C. and Isocarboxazid (6.8 g, molar yield of 83%, purity by HPLC 99.9%) was obtained as a white solid.

Method E

A reactor was charged at room temperature with methyl 5-methylisoxazole-3-carboxylate (15 g), benzylhydrazine dihydrochloride (31 g, potentiometric assay of 100%), n-heptane (75 ml) and toluene (75 ml). The suspension was heated to about 35° C. and triethylamine (32.8 g) was added slowly with a dropping funnel. At the end of the addition the temperature was adjusted to about 41° C. and maintained at that temperature overnight. After about 17 hours the temperature was lowered to 33° C. and water (60 ml) was added slowly with a dropping funnel. The suspension was cooled to room temperature, then filtered and washed with water (30 ml) and n-heptane (30 ml). The product was dried under vacuum at 50° C. overnight and Isocarboxazid (19.5 g, molar yield of 79%, purity by HPLC 99.6%) was obtained as a white solid.

Method F

A reactor was charged at room temperature with methyl 5-methylisoxazole-3-carboxylate (100 g), benzylhydrazine dihydrochloride (209.5 g, potentiometric assay of 99%) and n-heptane (1500 ml). To the suspension was added slowly with a dropping funnel triethylamine (218.8 g). At the end of the addition the temperature was adjusted to about 30° C. and maintained at that temperature overnight. After about 17 hours the suspension was cooled to 20° C. and water (600 ml) was added slowly with a dropping funnel. The suspension was filtered and washed with water (600 ml), isopropanol (2×200 ml) and n-heptane (400 ml). The product was dried under vacuum at 50° C. and Isocarboxazid (140.5 g, molar yield of 86%, purity by HPLC 99.4%) was obtained as a white solid.

Method G

A reactor was charged at room temperature with methyl 5-methylisoxazole-3-carboxylate (6 kg), benzylhydrazine dihydrochloride (12.4 kg, potentiometric assay of 89%) and n-heptane (90 Lt). To the suspension was added slowly triethylamine (12.44 kg). At the end of the addition the temperature was adjusted to about 30° C. and maintained at that temperature overnight. An in-process control sample taken after about 18 hours showed only 0.3% of residual methyl 5-methylisoxazole-3-carboxylate. The suspension was cooled to 20° C. and water (36 Lt) was slowly added. The suspension was transferred to a centrifuge. The isolated solid was washed with water (2×18 Lt), isopropanol (2×12.5 Lt) and n-heptane (2×12.5 Lt). Isocarboxazid (8.5 kg, purity by HPLC 99.1%) was obtained as off-white solid.

1H-NMR (300 MHz, DMSO-d6, 293 K): δ=2.44 (s, 3H, Ar—CH3), 3.98 (d, J=5.7 Hz, 2H, Ph-CH2-), 5.53 (dt, J=5.9, 5.7 Hz, 1H, Bz-NH—), 6.50 (s, 1H, Ar—H), 7.21-7.40 (m, 5H, C6H5-), 10.17 (d, J=5.9, 1H, —NH—CO—).

Example 2

Crystallisation of N'-benzyl-5-methylisoxazole-3-carbohydrazide (Isocarboxazid)

A reactor was charged with Isocarboxazid (25 g, purity by HPLC 99.4%) in glacial acetic acid (55 ml). A solution was obtained at 20-25° C. Charcoal (250 mg) was added and after about 30 min the suspension was filtered. The solution was added dropwise at room temperature into a reactor containing a mixture of water (188 ml) and isopropanol (62 ml). During the addition the product precipitates. The suspension was cooled to 10° C., then filtered, washed with water (2×50 ml) and dried at 50° C. overnight. Isocarboxazid (21.3 g, yield of 85%, purity by HPLC 99.9%) was obtained.

H-NMR (300 MHz, DMSO-d6, 293 K): δ=2.44 (s, 3H, Ar—CH$_3$), 3.98 (d, J=5.7 Hz, 2H, Ph-CH$_2$—), 5.53 (dt, J=5.9, 5.7 Hz, 1H, Bz-NH—), 6.50 (s, 1H, Ar—H), 7.21-7.40 (m, 5H, C$_6$H$_5$—), 10.17 (d, J=5.9, 1H, —NH—CO—).

The invention claimed is:

1. A process for preparing N'-benzyl-5-methylisoxazole-3-carbohydrazide (Isocarboxazid), which comprises
   a) reacting 5-methyl-3-isoxazole carboxylic acid ester (II), (II)

wherein R is a C$_{1-4}$ alkyl,
with benzylhydrazine or a salt thereof (III)

(III)

in an aprotic organic solvent and in the presence of an organic base.

2. The process according to claim 1, further comprising
   b) isolating the material as Isocaboxazid (I) and optionally
   c) re-crystallizing the isolated Isocaboxazid (I) obtained in step (b).

3. The process according to claim 1, wherein R in formula (II) is methyl.

4. The process according to claim 1, wherein the aprotic solvent is toluene, heptane, cyclohexane, isopropylacetate isopropyl acetate or a mixture thereof.

5. The process according to claim 1, wherein the organic base is triethylamine.

6. The process according to claim 1, wherein the reaction is performed at a temperature below 50°.

7. The process according to claim 6, wherein the temperature is in the range of 25° C. to 50° C.

8. The process according to claim 1, wherein the compound (III) is benzylhydrazine dihydrochloride.

9. The process according to claim 2, wherein the recrystallization is performed by dissolving the product obtained in step (b) in a solvent selected from acetone, methanol, acetic acid and DMSO, or a mixture thereof at a temperature between 20 and 40° C., followed by the addition of an anti-solvent selected from water, toluene, alkanes, and cycloalkanes, or a mixture thereof, or a mixture of water and isopropanol.

10. The process according to claim 1, wherein the amount of said aprotic solvent is in the range of 8 to 15 Volumes.

11. The process according to claim 1, wherein the ratio between said organic base and benzylhydrazine (III) is in the range of 1.9 to 2.2 mol/mol.

12. The process according to claim 5, wherein the ratio between triethylamine and benzylhydrazine (III) is in the range of 2.00 to 2.03 mol/mol.

13. The process according to claim 1, wherein the ratio of benzylhydrazine (III) and ester of formula (II) is in the range of 1.2 to 1.6 mol/mol.

14. The process according to claim 13, wherein the ratio of benzylhydrazine (III) and ester of formula (II) is about 1.5 mol/mol.

15. A process for the preparation of a pharmaceutical composition which comprises preparing N'-benzyl-5-methylisoxazole-3-carbohydrazide (Isocarboxazid) according to claim 1 and formulating said N'-benzyl-5-methylisoxazole-3-carbohydrazide (Isocarboxazid) into a pharmaceutical composition.

* * * * *

UNITED STATES PATENT AND TRADEMARK OFFICE
CERTIFICATE OF CORRECTION

PATENT NO. : 10,329,264 B2
APPLICATION NO. : 15/748209
DATED : June 25, 2019
INVENTOR(S) : Carla De Faveri et al.

Page 1 of 1

It is certified that error appears in the above-identified patent and that said Letters Patent is hereby corrected as shown below:

In the Claims

Claim 4, at Column 10, Line 60, please delete the term "isopropylacetate" at the end of the line.

Signed and Sealed this
Twentieth Day of August, 2019

Andrei Iancu
*Director of the United States Patent and Trademark Office*